(12) United States Patent
Kardos et al.

(10) Patent No.: US 10,232,173 B2
(45) Date of Patent: Mar. 19, 2019

(54) CONTACTLESS ELECTROPERMEABILIZATION ELECTRODE AND METHOD

(75) Inventors: Thomas Joseph Kardos, Aliso Viejo, CA (US); Stephen Vincent Kemmerer, San Diego, CA (US); Rune Kjeken, Oslo (NO); Kate Broderick, San Diego, CA (US); Jay McCoy, San Diego, CA (US); Michael P Fons, San Diego, CA (US)

(73) Assignee: VGX Pharmaceuticals, LLC, Plymouth Meeting, PA (US)

( * ) Notice: Subject to any disclaimer, the term of this patent is extended or adjusted under 35 U.S.C. 154(b) by 315 days.

(21) Appl. No.: 13/263,802

(22) PCT Filed: Apr. 16, 2010

(86) PCT No.: PCT/US2010/031431
§ 371 (c)(1),
(2), (4) Date: Oct. 10, 2011

(87) PCT Pub. No.: WO2010/121160
PCT Pub. Date: Oct. 21, 2010

(65) Prior Publication Data
US 2012/0046598 A1 Feb. 23, 2012

Related U.S. Application Data
(60) Provisional application No. 61/212,803, filed on Apr. 16, 2009.

(51) Int. Cl.
A61N 1/32 (2006.01)
A61N 1/04 (2006.01)
A61M 37/00 (2006.01)

(52) U.S. Cl.
CPC ............ *A61N 1/327* (2013.01); *A61N 1/0416* (2013.01); *A61N 1/0476* (2013.01); *A61M 2037/0007* (2013.01); *A61N 1/325* (2013.01)

(58) Field of Classification Search
CPC .... A61N 1/325; A61N 1/0416; A61N 1/0476; A61N 1/327; A61M 2037/0007;
(Continued)

(56) References Cited

U.S. PATENT DOCUMENTS 4,429,694 A * 2/1984 McGreevy ...................... 606/40
5,074,305 A * 12/1991 Guderian ............... A61N 1/326
361/232

(Continued)

OTHER PUBLICATIONS

Korean Final Rejection from the Korean Intellectual Property Office for Application No. 10-2011-7027142 dated Nov. 29, 2016 (4 pages).
(Continued)

*Primary Examiner* — Bhisma Mehta
*Assistant Examiner* — Laura Schell
(74) *Attorney, Agent, or Firm* — Baker & Hostetler LLP

(57) ABSTRACT

Devices and methods for delivering an electropermeabilizing pulse of electric energy to a tissue surface to enable delivery into cells in the tissue therapeutic substances. The device incorporates a source capable of generating a sufficient voltage potential to deliver a spark across a gap and delivers same to the tissue surface.

13 Claims, 12 Drawing Sheets

(58) Field of Classification Search
CPC ...... A61M 2205/054; A61M 2205/055; A61M 1/3669; A61M 2005/3283; A61M 2205/3538
USPC .................................................... 604/19, 20
See application file for complete search history.

(56) References Cited

U.S. PATENT DOCUMENTS

| | | | |
|---|---|---|---|
| 5,425,735 A * | 6/1995 | Rosen | A61B 17/22022 604/164.08 |
| 6,010,613 A | 1/2000 | Walters et al. | |
| 6,026,327 A | 2/2000 | Dervieux | |
| 6,261,301 B1 * | 7/2001 | Knesch | A45D 26/0023 606/131 |
| 6,413,256 B1 * | 7/2002 | Truckai et al. | 606/41 |
| 8,348,938 B2 * | 1/2013 | Blomgren et al. | 606/41 |
| 2002/0010414 A1 | 1/2002 | Coston et al. | |
| 2007/0021803 A1 | 1/2007 | Deem et al. | |
| 2007/0106349 A1 * | 5/2007 | Karni | A61B 18/042 607/101 |
| 2008/0091135 A1 | 4/2008 | Draghia-Akli | |
| 2010/0280513 A1 * | 11/2010 | Juergen | A61B 18/1477 606/41 |
| 2011/0009929 A1 * | 1/2011 | Nuccitelli et al. | 607/72 |

OTHER PUBLICATIONS

Korean Last Preliminary Report from the Korean Intellectual Property Office for Application No. 10-2011-7027142 dated Jan. 5, 2017 (10 pages).
Korean Preliminary Rejection from the Korean Intellectual Property Office for Application No. 10-2016-7036644 dated Apr. 5, 2017 (5 pages).
Office Action from the Canadian Intellectual Property Office for Application No. 2,756,276 dated Mar. 21, 2017 (6 pages).

* cited by examiner

CONTACTLESS ELECTROPERMEABILIZATION ELECTRODE AND METHOD

CROSS-REFERENCE TO RELATED APPLICATIONS SECTION

This application is a 371 National stage entry of International Application No. PCT/US2010/031431, filed Apr. 16, 2010, and claims the benefit of U.S. Provisional Application No. 61/212,803, filed Apr. 16, 2009, the contents of which are incorporated herein by reference.

FIELD OF THE DISCLOSURE

This disclosure relates to delivery of therapeutic substances including macromolecules, such as polynucleotides and polypeptides, into mammalian cells, particularly cells lying adjacent or otherwise near tissue surfaces, using a novel electropermeabilization system.

BACKGROUND

The following description includes information that may be useful in understanding the present disclosure. It is not an admission that any such information is prior art, or relevant, to the presently claimed inventions, or that any publication specifically or implicitly referenced is prior art.

Electropermeabilization of mammalian cells is a technique that has been used for delivery of therapeutic substances including small molecules, such as anticancer agents bleomycin and cisplatin, and macromolecules such as nucleic acids and proteins. Typically, delivery of such substances into cells is brought about by injecting the substance into the tissues containing the cells, which injection merely places such substance into the interstitial spaces between the cells, followed by physically contacting the tissues with a metallic electrode of one configuration or another and applying an electric potential across the electrodes. Usually, the electrode is manifest in the form of at least two opposing needle-like tissue piercing rods or tubes comprising an anode and a cathode. Other forms of tissue contacting electrodes include non-penetrating electrodes such as planar pads as found in "caliper" electrode devices such as disclosed in U.S. Pat. No. 5,439,440 and meander electrodes such as disclosed in U.S. Pat. No. 6,009,345. Still other electrode types have included minimally invasive electrodes such as disclosed in U.S. Pat. No. 6,603,998.

With regard to the electrodes as mentioned above, all operate within a paradigm well understood in the electrical arts to require express and direct contact between the electrode and the tissue undergoing electropermeabilization. Further, the electrical potential placed across the positive and negative poles, often expressed as "field strength" in Volts/centimeter, has been in the vicinity of tens to hundreds of volts per centimeter, i.e., voltage potential between the positive and negative poles spaced apart in, or on, the tissue a given distance. Typically, distances between electrodes are from tenths of centimeters to full centimeters of length. In most disclosures concerning electropermeabilization, the voltages required to provide a field strength sufficient for cell poration in the tissues are anywhere from one Volt for skin tissues to upwards of five or six hundred volts for cells lying in deeper body tissues. The various levels of voltage applied are typically dependent upon the spacing of the positive and negative electrodes and the electric resistance of the tissue undergoing treatment.

There have been many recent advances in the art of electropermeabilization wherein low voltage potentials have been applied to skin tissues. In many of these cases, the low voltage applied has been tied to very lengthy time periods for applying the electrical energy. In some cases, the electrical energy has been applied in a direct current form understood in the arts as providing an electrophoresis or iontophoresis effect wherein substances are moved through the tissue slowly. In such conditions and particularly with small molecules, the electric pulses only provide for the molecules to be moved through tissue interstitial space, not inside the cells within the tissue. Even where the low voltage has been applied for short periods of time, the electrodes comprise the typical complex two pole array arrangement, i.e., for example, at least one each of independently chargeable cathode(s) and anode(s) placed in contact with the tissues. Other recent disclosures discuss the use of very high voltages, in the 10,000 plus Volt range, for very short time periods to achieve delivery of substances into cells but none the less require contact of the electrodes with the tissue.

Whether using low or high voltages, tissue contacting electrodes systems are subject to practical limitations primarily concerning safety and comfort, or lack thereof, to the mammal undergoing treatment. There is also the practicality or impracticality of manufacturing complex miniaturized arrays containing both anodes and cathodes often organized to be pulsed independently of one another in various sequences and direction of pulsing. Use of high voltages with tissue piercing and surface touching electrodes can be dangerous for the potential of severe electric shock if conditions include high amperage over a time greater than 10 millisec. Use of low voltages over an extended period of time, though typically not dangerous, has the potential of being uncomfortable to the patient mammal or otherwise requires complex manufacturing processes. In addition, there are concerns that voltage facilitated systems or delivery methods result in low levels of efficacy.

Still other issues are of concern in delivery of substances to skin or tissue surface cells. For example, some systems disclose methods of delivering the substance through the skin surface, i.e., the stratum corneum, followed by delivery of the electric potential with the typical tissue penetrating or surface contacting electrodes. With regard to such substance delivery, instead of direct injection some systems attempt to draw the substance directly through the stratum corneum by iontophoresis and/or electrophoresis by applying various means to first ablate the stratum corneum before providing the substance and electric potential. For example, one system uses a laser beam to poke holes in the stratum corneum (U.S. Pat. No. 6,527,716). Another uses a high intensity tissue ablating spark not unlike a cauterizing surgical instrument (U.S. Pat. No. 6,611,706). In each of such systems, the methodology relies on physically disrupting the stratum corneum in order to deliver the substance and further aid in the transmission of the electrical energy from the tissue contacting electrodes into the tissue.

Thus, there is in the art a need to advance delivery of substances into cells using electropermeabilization in a manner that avoids electrical hazards, discomfort to the treated patient, damage to the tissues, and complex manufacturing.

SUMMARY

Disclosed herein is a novel methodology and electropermeabilization (or electroporation) device that delivers an electric potential having a sufficient field strength for causing cell permeability (or reversible pore formation) in skin-based or tissue surface-based cells without either causing potential hazardous electrical conditions, physical damage to the tissue surface, or noticeable discomfort. Further, the novel electrode is capable of delivering the necessary electric potential without being invasive, i.e., not penetrating the skin.

In one embodiment, there are disclosed methods of delivering therapeutic substances, which can include drugs, small molecules, and macromolecules to cells associated with tissue surfaces of a mammal, such as that of skin. With respect to skin, the current method can be used to deliver such substances into cells of epidermal and dermal tissue. As defined herein, macromolecules include large steroidal chemical compounds, as well as polynucleotides such as DNA, RNA, siRNA and the like, and polypeptides such as proteins comprising chains of amino acids between 8 and 3000 amino acid units. In an embodiment, polynucleotides include single and double stranded moieties, as well as both linear and circular polynucleotide sequences encoding polypeptides comprising whole functional proteins and fragments thereof, including short epitopes.

In one embodiment, there are disclosed methods of imparting a sufficient electric energy pulse (or electropermeabilizing electric voltage potential) to a tissue surface to cause reversible poration in cells of the tissue for the cellular delivery of a therapeutic substance into the porated cells. In another embodiment, there are disclosed methods of delivering the pulse of electric energy (or delivering or discharging the electric voltage potential) without the need for a tissue penetration, and preferably without contacting the tissue with the electrode or "non-contact." Thus, the electrode advances the art of imparting electroporative electric energy pulses to tissues for the purpose of causing electropermeabilization in that there need not be any trauma to the tissue, such as penetrating the tissue by a needle-like member, or alternatively, compressing, scratching, burning, or ablation of the skin surface other than the subcutaneous placement preelectropermabilization of the substance to be delivered to the cells.

In still another embodiment, the electropermeabilization system advances the delivery of electric energy by providing a novel route to electropermeabilization of cells for the direct delivery into the cells of the therapeutic substances in that present implementations provide a simplification of the electrode circuitry from the prior art requirement of two electrodes of opposing polarities at the delivery site in a tissue to instead, use of only a single electrode of a singular polarity at the delivery site that works in concert with (or otherwise discharging against) the polarity of the quiescent or grounded tissue of the subject being treated whether that is more positive or more negative relative to the delivering electrode polarity. In a further embodiment, the energy imparted to the tissue is dependent upon a combination of the potential of the voltage discharged and the distance or "gap" between the electrode tip and the tissue surface. In a related embodiment, the gap, rather than exist exclusively between the non-contact electrode and the tissue surface, can include a "spark-gap regulator" element located between the non-contact electrode and the device circuitry. The spark-gap regulator allows for discharge of the voltage potential in a predeterminable fashion limiting the amount of current relative to time. Furthermore, in this embodiment, the distal end of the electrode can be in contact with the surface of the tissue, i.e., can contact the surface of skin. In a related embodiment, the singular polarity of the non-contact electrode allows for reference not to "field strength" as is common in prior electroporation systems requiring electrodes of opposing polarity, but to "total energy" imparted to the tissue. In a further embodiment, the pulse of electric energy provided by the non-contact electrode can have a total electrical charge imparted into the tissue of about between $2.8 \times 10E-8$ and $2.5 \times 10E-6$ Coulombs to achieve electropermeabilization that is equivalent to between about 0.025 mJ and 270 mJ (millijoules) of energy, as further disclosed in Table I.

In another embodiment, an alternative single polarity electrode may comprise a tissue contacting array of noninvasive or alternatively minimally invasive electrodes comprising needle-like projections, in each case, all of a singular polarity. In an embodiment, the array can be constructed from a single electrically conductive material. As used herein a "single polarity electrode" or a "singular polarity electrode" is one that is constructed so as to possess only one pole, namely either anode or cathode, as the case may be. Where such a singular polarity electrode comprises an array of needle like projections, all such projection electrodes are pulsed in one pole from the electric energy generation source to the tissue. As used herein, a noninvasive electrode is an electrode comprising an array of needle-like projections that do not penetrate through a stratum corneum layer of skin tissue. As used herein, a minimally invasive electrode is an electrode array comprising needle-like projections that penetrate through a stratum corneum layer to a depth of subdermal tissue, i.e., about 1-2 mm. In this alternate embodiment, the electrode does contact tissue surface but energy imparted from the singular electrode derives from an electrical pulse driven across a spark-gap regulator as disclosed herein.

In some embodiments where the electrodes are minimally invasive or contact the surface of the tissue, the energy source can be one that is capable of generating a sufficient electric voltage potential over a period of time less than 1 millisecond, and preferably less than 100 microseconds. In preferred embodiments, the energy source is a piezoelectric crystal. In such embodiments, only one gap is necessary between the energy source and the tissue—such gap is between the electrode's distal end and the tissue. In some embodiments, the electrode can have a spark-gap regulator.

In another embodiment, there provided methods of delivering the electroporative pulse of energy in a regulated manner wherein the total energy discharge is controlled by a "spark-gap regulator". In an embodiment, the spark-gap regulator comprises an electrically neutral or nonconductive housing, such as clear plastic, encasing two electric leads separated by a "gap" of a predetermined measurement and of a predetermined electrical resistance rating and optionally under either positive or negative atmosphere pressure conditions, such as for example a vacuum or atmospheric pressure. In related embodiments, the spark-gap regulator provides the ability for the delivery system to be equipped with any of a variety of spark-gap regulators each manufactured to preset voltage thresholds for use in setting predetermined delivery parameters including such as minimum and peak voltages, current range, and total and/or net charges/energies (Coulombs or Joules) imparted into the tissue. It is contemplated that each of these parameters can affect the immune outcome for a particular disease or disorder being treated in the mammal.

In still another embodiment, the spark-gap regulator can be constructed to provide for any number of electrical energy levels (or electric voltage potentials) to be dischargable across the gap and thereby regulate the discharge of the voltage potential applied to the tissue via the electrode.

In some instances the electrodes include: contacting single polarity electrode array, or alternatively, the non-contact electrode.

In yet other embodiments, the energy source for providing a single polarity potential can comprise any of a 1 to 12 V battery, a charged capacitor, a charge coil, a piezoelectric crystal, or a Van de Graaff generator.

In further embodiments, there is provided methods of eliciting an immune response in a mammalian tissue by single polarity electropermeabilization.

Other features and advantages will be apparent from the following drawings, detailed description, and appended claims.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there are shown in the drawings example constructions of the embodiments; however, the embodiments are not limited to the specific methods and instrumentalities disclosed. In the drawings.

DETAILED IMPLEMENTATIONS OF THE DISCLOSURE

Figure 1:
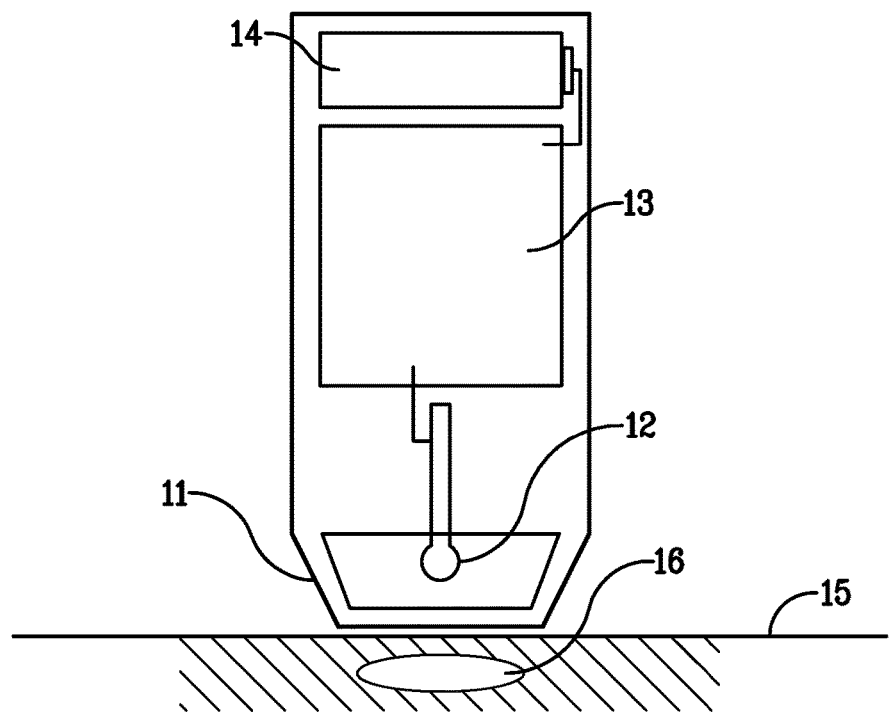
FIG. 1 is a schematic drawing depicting examples of elements of a device in accordance with the present disclosure.
Figure 2:
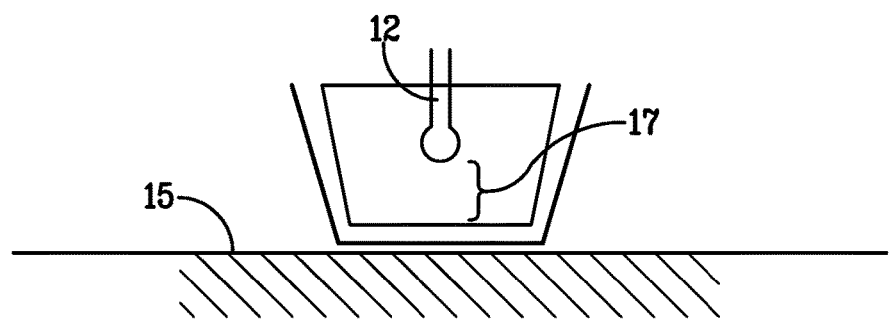
FIG. 2 is a close up representation of the non-contact singular polarity electrode separated by a "gap" from the tissue surface.
Figure 3A:
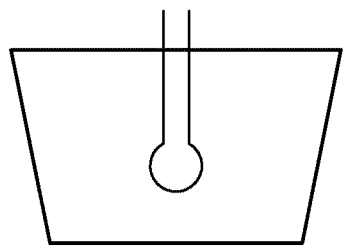
FIGS. 3A, B, and C are schematic depictions of three shapes that may be used for the non-contact singular polarity electrode.
Figure 3B:
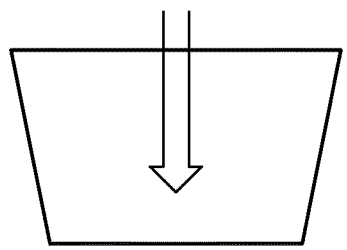
Figure 3C:
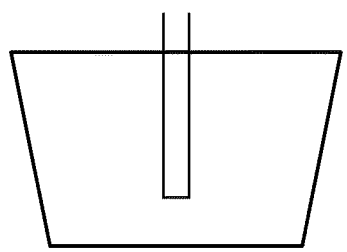

Provided herein are novel electropermeabilization (or electroporation) systems and methods for imparting electropermeabilizing electric pulses of energy to surfaces of tissues using a non-contact electrode, wherein the electrode does not contact the tissue, or a contact electrode wherein the electrode does contact the tissue with minimal penetration of skin, and preferable only surface contact.

FIG. 1 is a schematic drawing depicting examples of elements of a device 10 resting on a tissue surface 15 wherein there has been placed a bolus of therapeutic substance 16. The device has housing 11 containing an electric energy source 14, circuitry 13 and non-contact singular polarity electrode 12. The housing 11 forms a cowling around and extending a predetermined measurement greater than a length of the electrode 12.

FIG. 2 is a close up representation of the non-contact singular polarity electrode 12 separated by "gap" 17 from the tissue surface 15.

FIGS. 3A, B, and C are schematic depictions of three shapes that are useful for the non-contact singular polarity electrode. In FIG. 3A, the tip of the electrode is spherical. In FIG. 3B, the tip is pointed. In FIG. 3C, the tip is flat.

The term "sufficient voltage potential" or "voltage potential sufficient" when referring to the energy source and the voltage potential such source generates, the term refers to a minimum amount of voltage potential that is required to generate a spark that is able to jump across the gap in the electrode (i.e., the space gap of the spark-gap regulator), or the gap between the electrode and the surface of the tissue when spark-gap regulator, to deliver a desired charge to the tissue.

The term "predetermined distance" or "desired distance" when referring to the gap in the electropermeabilization system, refers to either the space gap of the spark-gap regulator or the gap between the distal end of the electrode and the tissue surface (when no spark-gap regulator is present). However, if both the space gap and the gap between electrode and tissue are provided in said system, neither gap will be larger than that of the predetermined distance. In embodiments where both gaps are present, the gap between the distal end of the electrode and the surface of the tissue will be the same or shorter than the space gap of the spark-gap regulator.

In a first embodiment, the device 10 can comprise an electrode 12 that need not contact the tissue surface 15 in order to impart into the tissue a pulse of electric energy sufficient to cause electropermeabilization of cells in the tissue. This ability to provide sufficient energy into the tissue without the electrode 12 touching the tissue 15 is a novel concept throughout the field of the electroporative arts. Moreover, the energy can be supplied to the tissue via the electrode 12 without causing any discernable damage, such as burning or ablation of the tissue surface 15. Rather, as concerns imparting energy to the stratum corneum, for example, the energy is imparted to the tissue with the stratum corneum remaining macroscopically intact. Specifically, the electric energy is applied directly to the tissue surface 15 at a location directly above or otherwise in the vicinity of a previously delivered bolus of therapeutic substance that has been injected just under the tissue surface 15. In an embodiment, the bolus is injected into a mammalian patient, such as a human, at any of subepidermal, subcutaneous, or intradermal locations. The electric discharge can be directed as single, or alternatively, a plurality of individual pulses to various portions of the tissue area containing the bolus. By macroscopically intact, it is meant that there is no discernable macroscopic histological damage or alteration to the stratum corneum.

In this first embodiment, the non-contact electrode 12 operates as a point discharge source wherein electric energy pulsed to the electrode from the system circuitry is discharged to the tissue surface 15 across a space (air) gap 17 of a predetermined measure. Specifically, the electric pulse is discharged via a spark jumping across the gap 17 into the tissue after which the electric energy dissipates through the tissue. Thus, the electrode 12 imparts a singular polarity static discharge into the tissue. The energy pulses can comprise from 1 to over 100 individual sparks imparted to the tissue surface 15 with the electrode tip resting from anywhere of 0.01 cm to 10 mm above the tissue surface. In an embodiment, the total energy passed to the tissues via the spark is sufficient to cause electropermeabilization of cells within the tissue but is not so great as to cause any discernable damage to the tissue or the tissue surface 15. Generally, the electric energy can be described as static electric pulses. Typically, in order to achieve transfer of the energy pulse from the electrode across an air gap 17 to the tissue surface 15 requires voltage potentials that are in the range of kilovolts. Although high voltage potentials alone suggest the possibility of danger or discomfort potential for the treated mammal, since the generation of high voltages is of a static electric nature, and because the discharge across the air gap 17 occurs in an extremely short time frame (nanoseconds), there is little current generated in the tissue to cause tissue damage despite amperages reaching meaningful values. Thus, the system provides for discharge of high voltage potential with little danger of injury to the patient. In an embodiment, the voltage potential can range from about between 5 kVolts to over 100 kVolts. The time frame of discharge can be about between 5 nanoseconds to 5 microseconds where the gap 17 between electrode and tissue surface is between 0.01 cm and 1 cm. Where, as in this embodiment, the gap 17 between electrode 12 and tissue surface 15 acts as a defacto spark-gap regulator, i.e., there is no separate spark-gap regulator in the upstream circuitry, the gap 17 can be up to 1 cm without the resultant current flow becoming too great for both safety and sensation concerns. Within this gap range, in each instance the imparting of electric energy is barely perceptible.

Various sources of electric energy can be used to generate the voltage potentials for the non-contact electrode 12. The electropermeabilizing electric pulse is repeated a multiplicity of times between 2 and 20 pulses. For example, a Van de Graaff apparatus can be used to generate static electric potentials wherein a metal dome acts as a capacitor for building charge of between 5 kVolts and 100 kVolts that can be channeled through the circuitry 13 to the electrode for a discharge period of about between 5 nanoseconds and 5 microseconds. Alternatively, a piezoelectric crystal can be used wherein an impact mechanism can create high voltage short duration pulses of 20 to 100 nanoseconds. In yet another alternative, a high voltage Tesla coil with a transformer and switch can be arranged wherein a primary coil can be used to induce a secondary coil to a 5 kVolts to 100 kVolts potential over a period of 40 to 100 nanoseconds. In still another alternative, a 1, 3, 9, or a 12 Volt battery, for example, can be used to charge a capacitor to build voltage potentials of 100 volts to 1 kilovolt which can be discharged across the primary coil of a non-contact electrode 12 to the tissue surface 15 or alternatively via a spark-gap regulator (see, FIGS. 4A and 5) to a single polarity tissue contacting electrode 12. Finally, an alternating current source can be used in connection with a transformer to build the static voltage potential and operate as disclosed herein in singular polarity form. One of ordinary skill in the electric arts will understand details of how appropriate circuitry can be arranged to use these and other electric energy generators to build an appropriate voltage potential and to send the potential to the non-contact electrode 12 directly or first through a spark-gap regulator for added electrical discharge control.

In some embodiments where the electrodes are minimally invasive or contact the surface of the tissue, the energy source can be one that is capable of generating a sufficient electric voltage potential over a period of time less than 1 millisecond, and preferably less than 100 microseconds. In preferred embodiments, the energy source is a piezoelectric crystal.

Using any of the different electric energy sources noted herein, the discharge of the electric energy will occur naturally across the spark-gap regulator, or otherwise across the gap 17 from the non-contact electrode 12 to the tissue surface 15, in an oscillatory fashion such that the polarity of the pulse actually reverses in nanosecond time frames. Such discharge likely moderates the power intensity of the pulse thereby keeping the sparked voltage potential from burning, ablating or otherwise damaging the tissue surface 15.

Figure 4A:
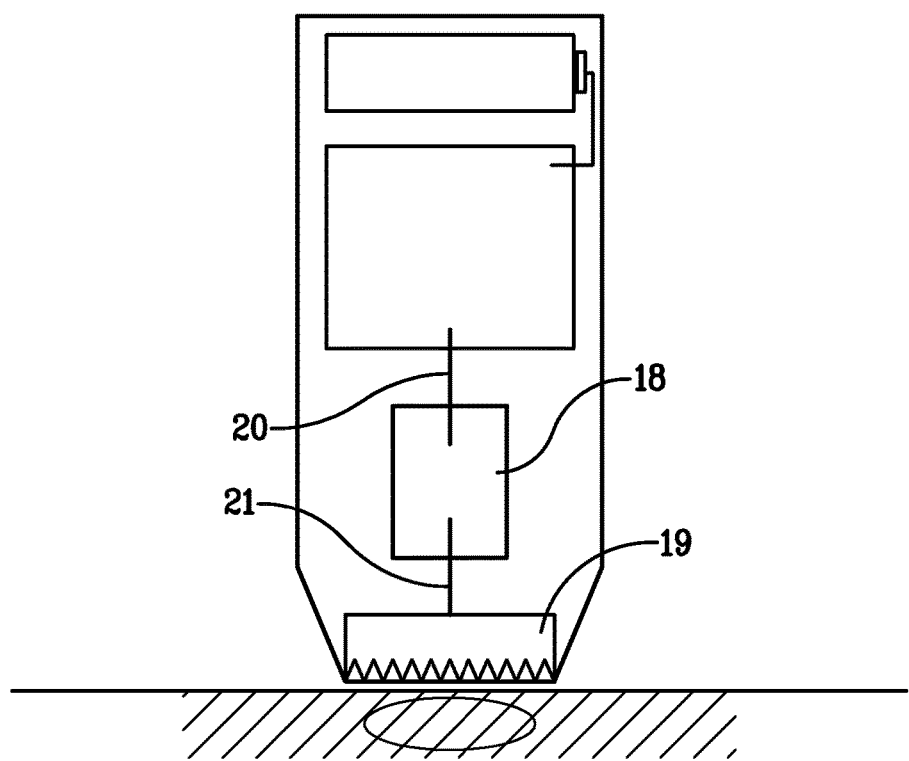
FIGS. 4A and B are schematic drawings depicting examples of elements of alternate designs of the device of FIG. 1.
Figure 4B:
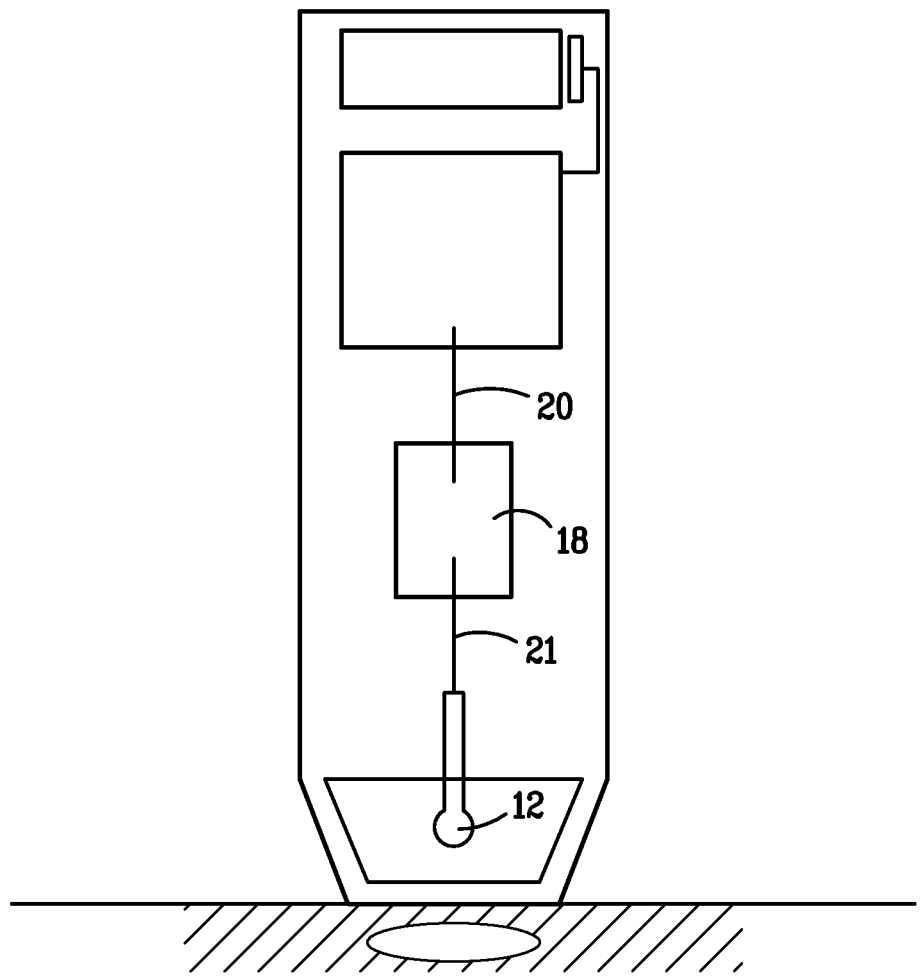

FIGS. 4A and B are schematic drawings depicting examples of elements of alternate designs for the device wherein the singular polarity electrode comprises either a tissue contacting single polarity electrode array 19 that is connected to a spark-gap regulator 18 as shown in FIG. 4A, or alternatively comprises a non-contact electrode 12 connected to a spark-gap regulator 18 as depicted in FIG. 4B.

With respect to the regulation of the total energies imparted to the tissue using the non-contact electrode, the energies sufficient for electropermeabilization can be tailored by adjusting the measure of the gap between the tip of the non-contact electrode and the tissue surface, or alternatively the measure of the gap of a spark-gap regulator, or alternatively adjusting the combination of a gap in the spark-gap regulator within the circuitry and the gap between the tissue surface and non-contact electrode. As an example, the system electronics and electrode can be arranged such that the gap between the non-contact electrode and the tissue surface is not the only location for regulation of voltage discharge. Rather, the non-contact electrode can have a spark-gap regulator upstream from the non-contact electrode, as depicted in FIG. 4B, so as to set the discharge regulation away from the non-contact electrode/treatment zone. This is similar to the alternate arrangement wherein the single polarity tissue contacting electrode array is connected to a spark-gap regulator upstream as shown in FIG. 4A.

Spark-gap regulation for electroporation allows for delivery of extremely short and high intensity voltage pulses without danger to the treated mammal and without macroscopically affecting the stratum corneum. The minimal gap distance can be calculated for setting voltages for use in electroporation. For example, at 1 atmosphere (760 torr) and room temperature (20 degrees Celsius), based on Paschen's Law and the Townsend breakdown mechanism in gases, as understood by one of ordinary skill in the art, where N is the density of air, "d" is the gap measurement, under the formula Voltage=K(Nd), the breakdown voltage necessary to cross a gap of the measurements is disclosed in Table I. The spark-gap regulator can be adapted for discharging an electric potential of about between 0.9 and 109 kV to the electrode.

Figure 5:
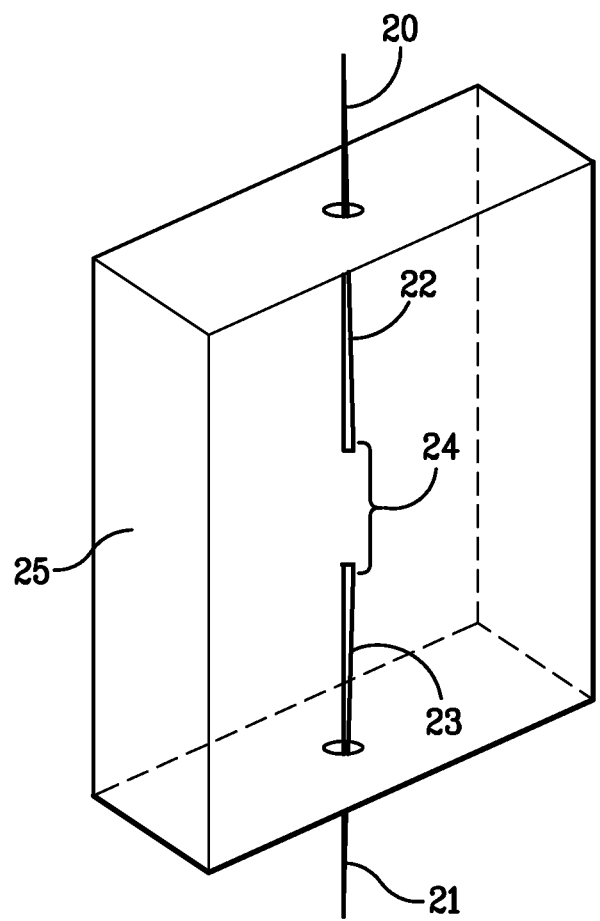
FIG. 5 is a three dimensional view of a spark-gap regulator.

FIG. 5 is a three dimensional view of a spark-gap regulator wherein electric leads 22 and 23 are separated by a gap 24 of a predetermined measurement inside housing 25. As shown in FIG. 5, the spark-gap regulator is a device comprising a housing 25, which is constructed of an electrically inert material such as glass, Plexiglas or clear plastic, enclosing each of two wires, a lead wire 20 and a receiving wire 21, electrically isolated from one another, placed so that there is a gap 24 separating terminal ends 22 and 23, respectively, thereof. The housing is constructed so that there can be a vacuum space, if desired, comprising the gap 24. This vacuum aspect provides for the allowance of any discharge of electric energy between the terminal ends 22 and 23 of the wires across the gap to occur without atmospheric molecules influencing the resistance of electric charge transfer across the gap. In this manner, the gap can be constructed to have any length measurement practical for use in sparking charge from the lead to the receiving wire and thereby specifically controlling the amount of energy that can discharge across the gap. Typically, the gap can measure about between 0.01 and 4 cm.

Figure 6A:
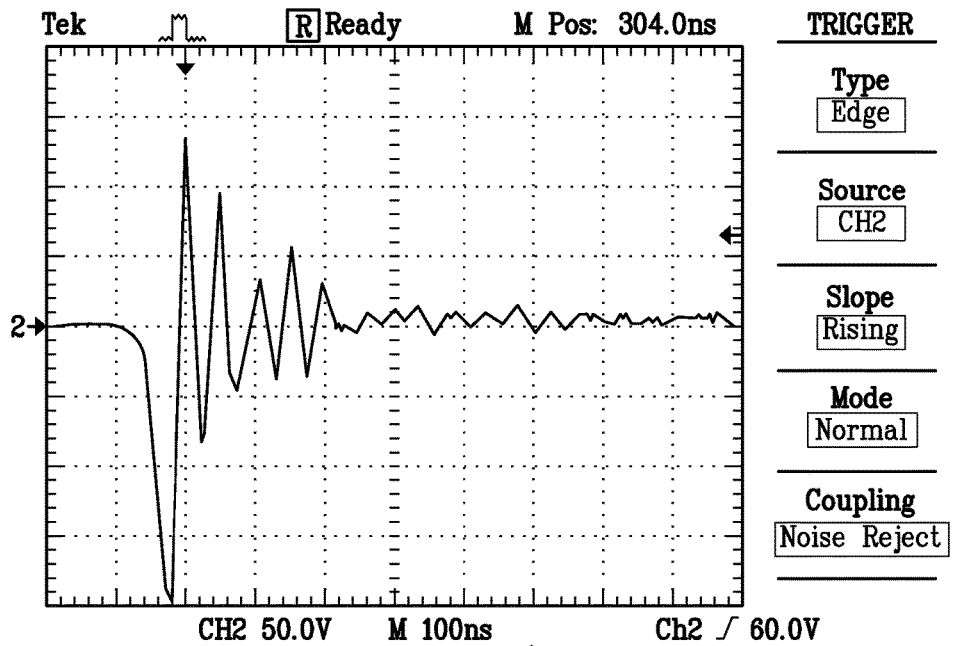
FIGS. 6A, B, and C are graphs depicting the pulse characteristics of electrostatic discharges from various energy sources.
Figure 6B:
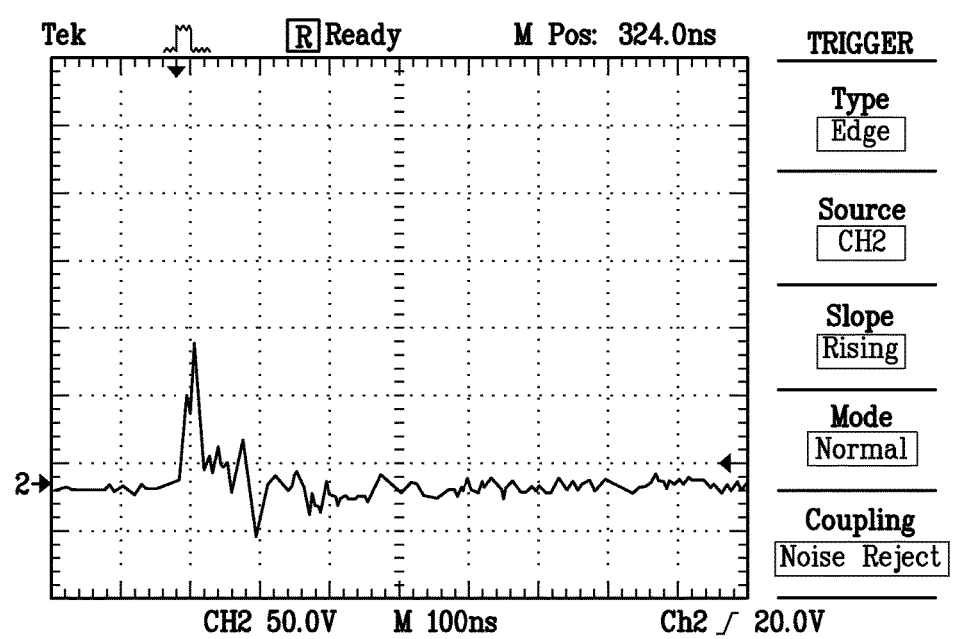
Figure 6C:
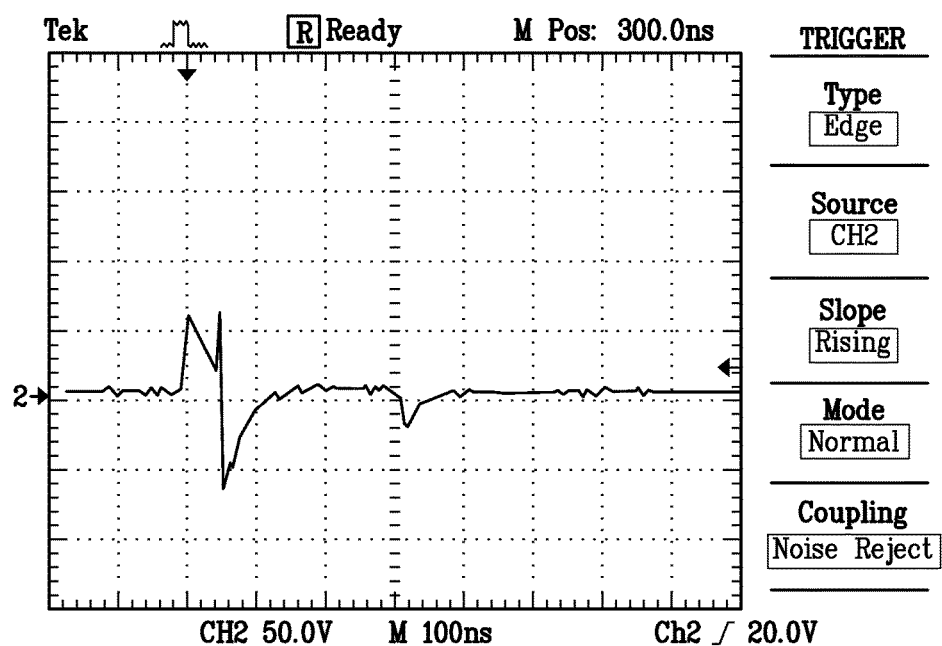

FIGS. 6A, B, and C are graphs depicting the pulse characteristics of electrostatic discharges from various energy sources. FIG. 6A is a graph of the discharge from a Van de Graaff generator, FIG. 6B is a graph of the discharge from a piezoelectric crystal, and FIG. 6C is a graph of the discharge from a spark coil. Each of the Figures illustrates time vs. voltage.

As depicted in FIG. 6A, the discharge of a pulse from a Van de Graaff generator occurred across about 40 nanoseconds in a sinusoidal fashion, each polarity having a pulse of between about 2 and 5 nanoseconds. The discharge of a piezoelectric crystal provided a similar sinusoidal discharge as shown in FIG. 6B. In this case, the bipolarity of the sinusoidal discharge occurred in a little over 10 nanoseconds. In still another example of electric pulse source discharge, a discharge across an air gap using a spark coil (step up transformer) is shown in FIG. 6C. In this instance, the discharge is even shorter on the order of 10 nanoseconds but here, the discharge is in a single broad sinusoidal spike. Thus, the spark coil generated discharge has inherently longer singular pulses of either polarity. The longer the single pulse, the more association with damage to tissue is observed. In an embodiment, the Van de Graaff and piezoelectric generated potential and discharge provides superior results in causing no discernable effect on the tissue surface while generation from a spark coil has the potential of being associated with effects on tissue if the total energy of the potential is higher than a predeterminable level. Therefore, the sparks, however generated, are those that can be generated and discharged into tissue surface without either purposely or inadvertently causing damage to the integrity of the stratum corneum.

Figure 7A:
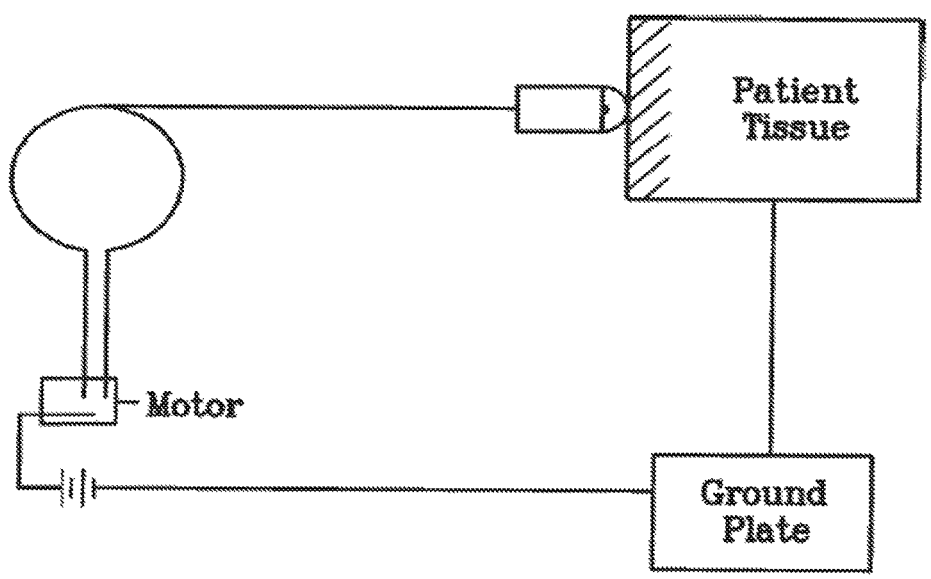
FIGS. 7A to F are drawings of various example electric circuits generally laying out the charge generation elements of alternate embodiments.
Figure 7B:
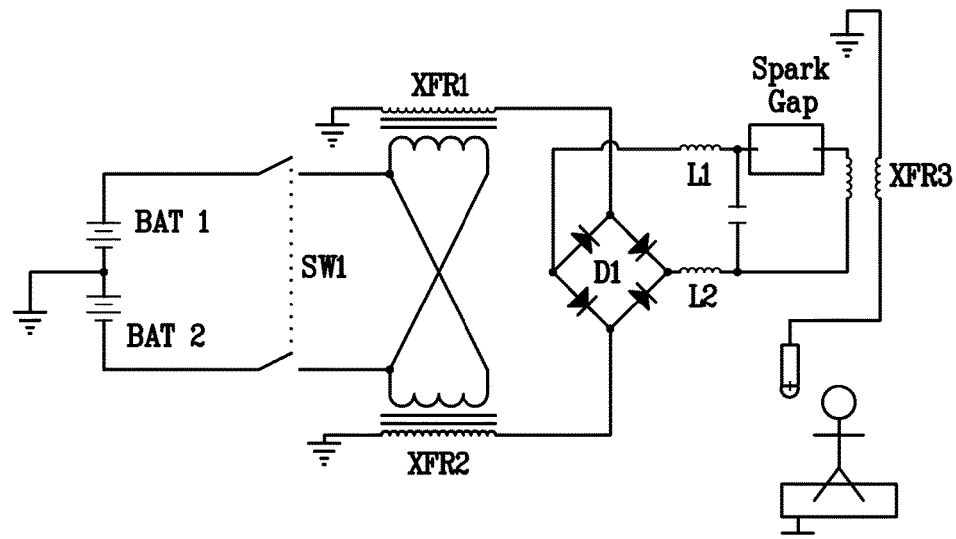
Figure 7C:
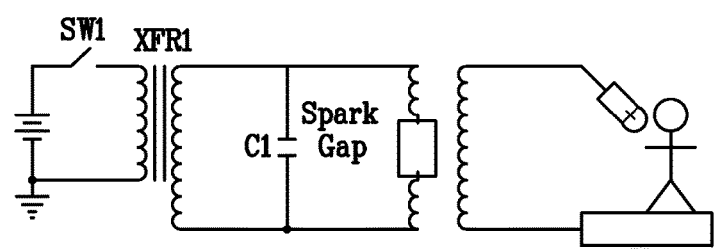
Figure 7D:
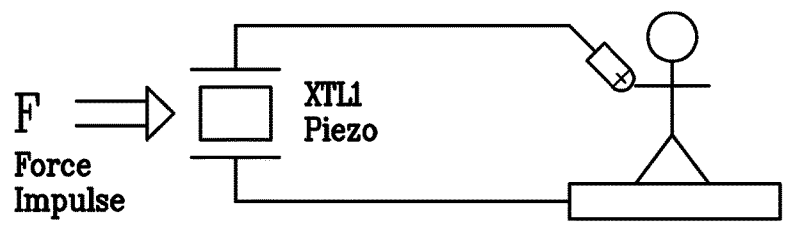
Figure 7E:
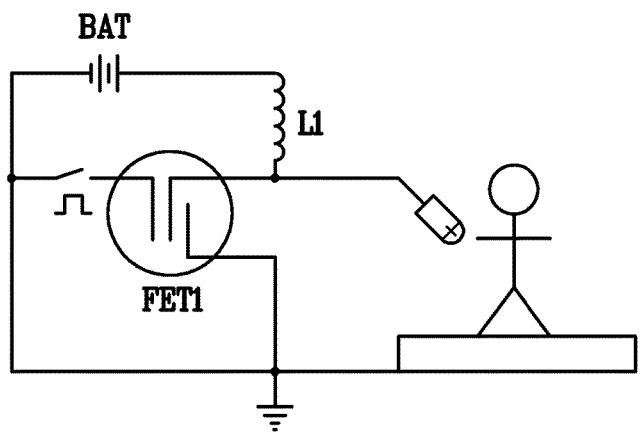
Figure 7F:
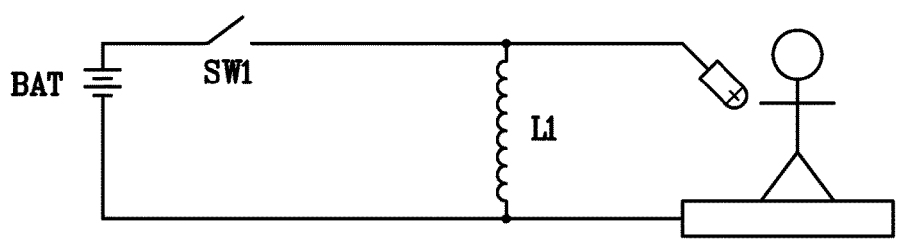

FIGS. 7A to F are drawings of various electric circuits generally laying out the charge generation elements of alternate embodiments. In FIG. 7A, a Van de Graaff generator system is depicted wherein charge buildup is delivered to the patient tissue directly with a non-contact single polarity electrode and a ground plate. This system can also include a spark-gap regulator if desired. In FIG. 7B, a battery power source can be arranged to step up voltage and send charge through a spark-gap regulator to the patient tissue. In FIG. 7C, a simpler circuit is disclosed wherein the charge generated is sent through a spark-gap regulator to the patient tissue. In FIG. 7D, a circuit wherein the charge is generated using a piezoelectric crystal is disclosed. Here the charge can be sent directly to the non-contact electrode or can be sent through a spark-gap regulator before being sent to the patient tissue. In FIG. 7E, a circuit is disclosed depicting a high voltage Field Effect Transistor (FET) switched coil. In FIG. 7F, a circuit is disclosed depicting a manually switched coil.

A Van de Graaff generator circuit can be relatively simple, using as basic components a circuit comprising a Van de Graaff generator attached to the non-contact electrode element such that the charge potential generated is regulated in its delivery to the tissue by gapping across the space between the non-contact electrode and the tissue surface. Alternatively, the charge potential can be sent to a spark-gap regulator and then on to the tissue via either the non-contact electrode or the tissue contacting single polar array electrode. There need not be any counter electrode. Rather, the system inherently provides for delivery of energies that will discharge through the body tissue into the environment. An alternative to using no counter electrode can be the use of a ground plate or an electrically conductive foot pad to assist complete discharge of energy through the body. Further, given that there is a lower net total charge imparted to the tissue via the Van de Graaff generated pulse (likely associated with the oscillatory nature of the static discharge, as shown in FIG. 6A), there is even less concern for needing a counter electrode to dissipate the imparted electric potential.

FIGS. 7B and C depict circuits that incorporate spark-gap regulators. These circuits are compatible with either the non-contact electrode or the single polarity tissue contacting electrode. In FIG. 7B, batteries "Bat 1" and "Bat 2" are connected to the primary coils of "xfr 1" and "xfr 2" by switch SW1 wherein the secondary windings of xfr 1 and xfr 2 are greater than their respective primary windings by the same ratio with respect to the voltage in the secondary windings as compared to the voltage of Bat 1 and Bat 2. These secondary windings are rectified by diode D1, and connect to additional coils L1 and L2 which further increase the voltage sufficient to jump the gap in the "spark-gap" unit which drives the primary coil of "xfr 3" to induce the final voltage seen by the spark electrode on the patient who is grounded to the environment. In this configuration, the spark-gap can be as little as 0.01 cm. In FIG. 7C switch SW 1 transfers battery voltage to the primary coil of xfr1 and the secondary coil of xfr 1, which is larger than the primary coil, and connects to a spark-gap regulator embedded within the primary coil of the output transformer, thereafter leading to the patient.

FIG. 7D is a drawing representing a circuit employing a piezoelectric crystal. Like the Van de Graaff generator, the charge pulse can be sent directly to the non-contact electrode or can be sent through a spark-gap regulator to a single polarity tissue contacting electrode. Also, as with the Van de Graaff generator, there need not be a return electrode but alternatively a grounding means, such as a conductive pad for example, on which the treated mammal stands can be used if desired.

FIGS. 7E and F depict coil voltage potential generator circuits. In FIG. 7E a high voltage field effect transistor (FET) switched coil is disclosed. Here, when a pulse is applied to the base of the FET 1 as diagrammed by closing a switch, the coil L1 is switched to ground and current begins to flow from the battery (Bat) through L1. When FET 1 turns off, current tries to continue through the inductive coil of L1 but cannot, and will trigger a spark through the patient until the energy stored up in L1 dissipates. Similarly, FIG. 7F shows a manually switched coil wherein the same mechanism occurs when the switch is opened after the coil has built up charge.

Figure 8A:
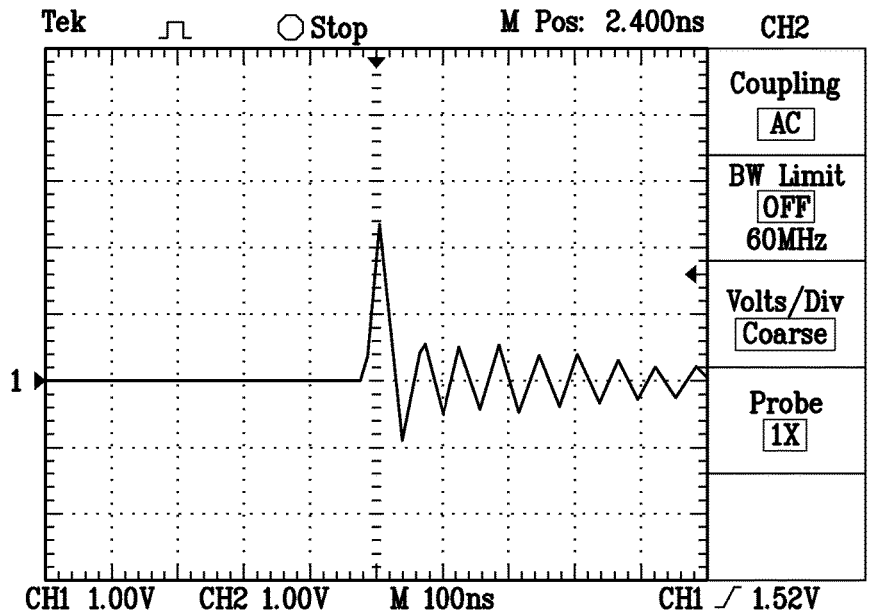
FIGS. 8A and B are graphs showing pulse discharges using a Van de Graaff generator.
Figure 8B:
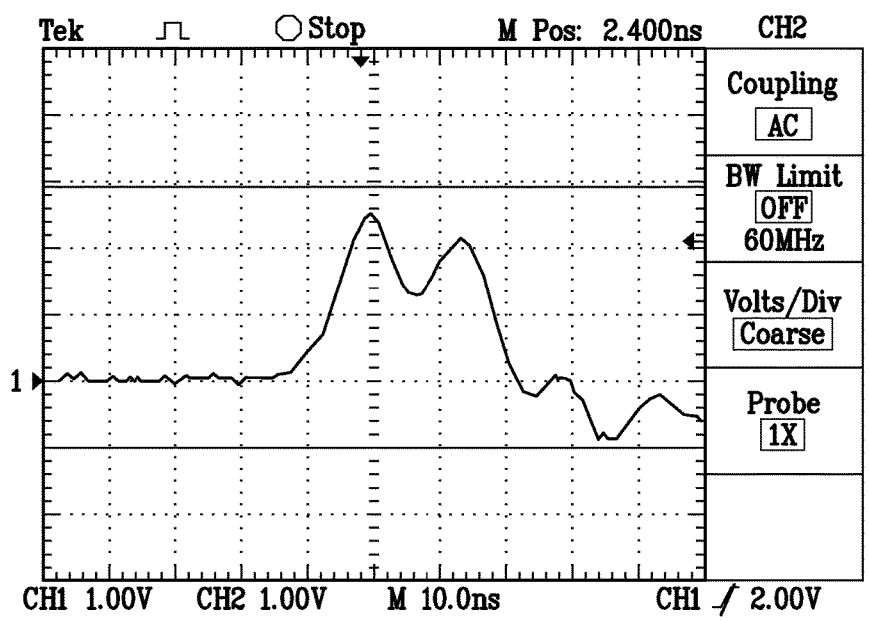

FIGS. 8A and B are graphs showing pulse discharges using a Van de Graaff generator. In FIG. 8A, the pulse is depicted wherein there are 100 nanoseconds per division in the graph. There are about 500 nanoseconds of a diminishing pulse at about 1 Volt per division. This translates to 10 Amps per division or a 25 Amp maximum current. This example has an initial pulse spike lasting about 30 nanoseconds. In FIG. 8B, the same section of the pulse is shown in 10 nanosecond increments showing the about 30 nanosecond nature of the initial pulse spike.

In further related embodiments, as shown in the example of FIGS. 8A and B, the discharge from a Van de Graaff generator is actually an oscillating discharge wherein there is a reversal of the spark polarity with reversals of charge flow in diminishing switchbacks until the energy, as measured in volts, falls below that value allowing jumping of the charge across the gap. The oscillating charge flow across the gap can occur lower than the initial gap cutoff value due to the charge flow across the air gap becoming a plasma. The observed discharge then continues in oscillations running out to about 1 millisecond even though the initial first pulse occurred in less than 40 nanoseconds.

In still other embodiments, the discharge of the electric potential can be sent into the tissue using an alternate to the non-contacting electrode, namely through a singular polarity tissue contacting electrode. In this alternate embodiment, rather than a spark directly to the tissue surface, the energy is directed to a single polarity array of needle-like projections after passing across an upstream spark-gap regulator. In an embodiment, the needle-like projections are either of a non-invasive type or alternately, of a minimally invasive type. Further, the singular polarity electrode can be fashioned from a simple single block of electrically conductive material. In a related embodiment, the array of "pins" or needle-like projections can comprise an array of various dimensions such as, for example, 1 to 100 pins arranged in a grid such as a 4×4 array or alternatively a 10×10, or any other configuration or shape, such as a square grid or a circular grid.

In either alternate embodiment of the electrode, i.e., either the singular polarity non-contact spark electrode, or the tissue contacting singular polarity array, as one of skill in the electric arts will recognize, there is a need for the voltage potential to discharge through the tissue and, ostensibly, find its way to a zero potential. This can be accomplished by either placing a discharge plate, essentially an opposite polarity electrode, in contact with the treated mammal, or preferably, providing for the imparted charge to become grounded in the tissue of the treated animal itself. Not in contrast with this physical need for the voltage potential to fully discharge from the site of entering the tissue, there is not a requirement for there to be located an electrode of opposite potential near the site of delivery of the singular polarity discharge that is delivered from the electrodes. The treated mammal should be grounded sufficiently to allow the static charge imparted to the mammal to reach ground potential. This can be accomplished by the imparted potential dissipating throughout the mammal's body tissues, or alternatively, a remote electrically conductive material can be placed in contact with the mammal's body, such as an electrically conductive foot pad.

For calculating the values in Table I, the majority of the discharge, whether using a Van de Graaff generator, a piezoelectric crystal, or a Tesla coil, occurs at the front end of the pulse (as shown in FIGS. 8A and B). Thus, taking the values obtained from the front end pulse spike, Amps, Coulombs, and total energy may be determined that is imparted into the tissue occurring from a variety of starting voltage potentials. For example, a positive charge having a 20 Amp peak current and lasting approximately 40 nanoseconds (Amps×pulse length=Coulombs) equals approximately $8.0 \times 10E^{-7}$ Coulombs for a 10 mm gap. Each of the values in the Table I were calculated similarly as one of ordinary skill in the art will understand.

TABLE I

| Gap in millimeters | Minimum K Volts to breach gap (breakdown) | Pulse Width (nanoseconds) | Representative Current Across gap (Amps) | Total Charge from electrode (Coulombs) | Net Energy to tissue (Joules) |
|---|---|---|---|---|---|
| 0.1 | 0.9 | 7 | 4 | $2.8 \times 10E-8$ | 0.000025 |
| 1 | 4.3 | 10 | 11 | $1.1 \times 10E-7$ | 0.00047 |
| 2 | 7.6 | 12 | 15 | $1.8 \times 10E-7$ | 0.0014 |
| 5 | 16.4 | 29 | 16 | $4.6 \times 10E-7$ | 0.0076 |
| 10 (1 cm) | 30.3 | 40 | 20 | $8.0 \times 10E-7$ | 0.024 |
| 15 | 43.8 | 40 | 22 | $8.8 \times 10E-7$ | 0.039 |
| 20 (2 cm) | 57.0 | 40 | 29 | $1.2 \times 10E-6$ | 0.066 |
| 25 | 70.2 | 40 | 35 | $1.4 \times 10E-6$ | 0.098 |
| 30 (3 cm) | 83.2 | 40 | 38 | $1.7 \times 10E-6$ | 0.14 |
| 35 | 96.1 | 40 | 60 | $2.4 \times 10E-6$ | 0.23 |
| 40 (4 cm) | 109.0 | 35 | 70 | $2.5 \times 10E-6$ | 0.27 |

Values based on 1 Atm (760 torr) at 20 degrees C., based on Paschen's Law, Townsend breakdown mechanism in gases, V = K (Nd), N = air density, d = gap; Current measured with Pearson Model 411 Current Meter, calibrated at 0.1 V/Amp. Spark generated via Van de Graaff generator. Formula Q(Coulombs) = amps X t(seconds); E(Joules) = Q x V.

Specifically, the minimum electric energy necessary to cross a gap of a given distance using a Van de Graaff generator is disclosed in Table I. With that minimum voltage potential, the minimum pulse length and the minimum current can be calculated as disclosed. Further, the total charge, in Coulombs, discharged across the gap can be calculated. Thus, there is an ability to graph the actual discharge, and calculate the net energy, in Joules, imparted into the tissue. From this Table I, the minimal energies capable of being delivered to the tissue surface for any given gap employed in the device can be determined whether the electrode to tissue surface gap and/or the upstream spark-gap regulator is used. This spark-gap regulation is useful for the alternate embodiments, e.g., the non-contact electrode and the tissue contacting electrode array. In both instances, singular polarity voltage potential discharge can be administered with a known total energy delivery on demand. Since that discharge will take place over a pulse period of approximately between 5 nanoseconds and 5 microseconds, there is no potential harm to the treated mammal. This short pulse time period allows for current of 4 to 70 Amps at very low total energies between about 0.00001 and 0.5 Joules without any significant danger to the treated mammal despite the high voltage levels associated with discharge across the gap.

For example, a Van de Graaff generator, such as for example, one chargeable to between 75 kVolts and 100 kVolts, was charged to 100 kVolts and the charge discharged through the spark-gap was calculated to be about $10^{-5}$ Coulombs. Specifically, as charge builds up on the large metal head of the Van de Graaff generator, which acts as a capacitor across the dielectric of air over a spark-gap of approximately 4 cm, a breakdown will occur over this gap once the voltage becomes over about 100 kVolts. Upon the breakdown and charge beings delivery across the gap, air ionizes between the electrode head and the skin/tissue of the mammal subject, and current begins to flow until the charge from the Van de Graaff equalizes with the static potential of the tissue. However, since the flowing current has inertia, the equal potential point between the Van de Graaff head and tissue will reverse, and build up an opposite relative charge as compared to the time when the breakdown initiated. There will be several oscillations of potential reversal as current flows back and forth, until the potential difference drops below a minimum to keep the spark-gap air ionized, at which time the spark event terminates.

In a similar fashion, calculations of energies imparted into the tissue can be made for voltage potentials generated from both piezoelectric crystals and Tesla coils as shown in Tables II and III, respectively, below. In these tabular calculations conditions for calculating were 1 atmosphere (760 torr), 20 degrees Celsius, based on Paschen's Law, Townsend breakdown mechanism in gases; V=K (Nd), N=air density, d=gap; current measured with Pearson Model 411 Current Meter, calibrated at 0.1 V/Amp. Q (Coulombs)=I (amps)×t (seconds), E (Joules) =Q×Volts.

TABLE II*

| Gap (mm) | K volts (breakdown) | Initial pulse width (nanosec) | Current (Amps) | Charge (Coulombs) | Energy (Joules) |
|---|---|---|---|---|---|
| 1 | 4.3 | 10 | 6 | 6.0 × 10E−8 | 0.00026 |
| 2 | 7.6 | 14 | 10 | 1.4 × 10E−7 | 0.0011 |
| 5 | 16.4 | 17 | 15 | 2.5 × 10E−7 | 0.0041 |
| 10 (1 cm) | 30.3 | 30 | 18 | 5.4 × 10E−7 | 0.016 |

*Piezoelectric crystal generator

TABLE III**

| Gap (mm) | K volts (breakdown) | Initial pulse width (nanosec) | Current (Amps) | Charge (Coulombs) | Energy (Joules) |
|---|---|---|---|---|---|
| 1 | 4.3 | 13 | 2 | 2.8 × 10E−8 | 0.00012 |
| 2 | 7.6 | 14 | 2.5 | 3.5 × 10E−8 | 0.0026 |
| 5 | 16.4 | 15 | 6 | 9.0 × 10E−8 | 0.0015 |
| 10 (1 cm) | 30.3 | 20 | 14 | 2.8 × 10E−7 | 0.0085 |

**Tesla coil generator

For example, calculations on total energy imparted were carried out using a Pearson inductive current monitor (Model 411, Pearson Electronics, Inc., Palo Alto, Calif. USA) that develops a 0.1 Volt/Amp voltage current ratio, and a Tektronix TDS210 oscilloscope (Tektronix, Inc., Beaverton, Oreg., USA) with a piezoelectric crystal that was capable of generating a 1 cm spark length, resulted in the generation of 25 Amps over a 20 nanosecond pulse to deliver about $10^{-6}$ Coulombs of electric charge. Specifically, I=dQ/dt with 1 Coulomb =1 Amp×1 Sec results in 25 Amps×20× $10^{-9}$ sec=0.5×$10^{-6}$ Coulombs.

In another example, using the formula I=delta Q/delta t, which can also be written as dQ=I×dt=V/R×dt, where I=current, Q=energy in Coulombs, V=volts, R=resistance in ohms, and t=time, using a piezoelectric crystal, a current of 10 Amps is generated over a 100 nanosecond pulse and a total charge transfer of $10^{-6}$ Coulombs. Specifically, the tip of the piezoelectric generator, which is conductive, such as an electrically conductive metal, and in contact with one side of the piezoelectric crystal, is brought within about 1 cm of the skin/tissue of the mammal subject. The other side of the piezoelectric crystal is connected to another electrical conduit that is subsequently grounded to the environment of the subject mammal wherein the grounded subject is in electrical communication with this second side of the crystal circuit. Upon mechanical impulse being applied to the crystal, a high voltage pulse between 15 and 35 kVolts is generated. This pulse, directed to the electrode head, and positioned about 1 cm from the tissue will be at an electrical potential with respect to the grounded subject that is sufficiently high to ionize the air gap between the nearest point of the test subject tissue surface to the electrode. Further, current will flow until the current built upon the crystal by the mechanical impulse dissipates.

As noted above, FIGS. 6A, B and C show the discharge of voltages from three different sources of power generation. In FIG. 6A, discharge from a Van de Graaff is shown wherein the discharge actually comprises an oscillating wave form. Thus, the total energy imparted to the tissue not only occurs in less than about 40 nanoseconds, it is actually a net of opposite polarities oscillating into the tissue. Further, the pulse period for each pulse polarity is extremely short, namely about 2 to 5 nanoseconds. Similarly, as shown in FIG. 6B, discharge of a piezoelectric crystal naturally occurs in a somewhat oscillatory fashion, again each polarity of the pulse being very short, about 2-5 nanoseconds. Still further, as shown in FIG. 6C, the discharge from a spark coil also exhibits an oscillation in the actual discharge but in this instance, the waveform comprises single long pulse periods in either pole of the oscillation, a phenomenon different from the discharge occurring from the Van de Graaff or piezoelectric crystal generators. The discharge from a spark coil generator, if too high a voltage potential, can cause tissue damage. Thus, when using a spark coil as a generation source, the system is tailored to discharge only energies sufficient for electropermeabilization and not damage tissue.

EXAMPLES

A. Non-contact Electrode Experiment

A device comprising a Van de Graaff generator as a power source and a non-contact electrode was placed 1 cm above a mammalian tissue surface (guinea pig) was pulsed with either 4 or 8 spark discharges across the 1 cm gap and above a 50 ul (microliter) bolus of previously delivered intradermal injection of green florescent protein (2 mg/ml dna plasmid in PBS) expressing plasmid (plasmid pgw12-GFP from Aldevron, N. Dakota). The spark-gap used with the Van de Graaff generator is approximately 1 cm, resulting in repeated sequence of 4 or 8 sparks of approximately 30 kVolts, resulting in delivery of approximately 25 milliJoules of energy during each spark event. If electropermeabilization has taken place and the plasmid entered the cells in the epidermal tissue, the protein encoded by the plasmid will be expressed and the green florescent protein will fluoresce under UV light.

In this experiment, the non-contact electrode was placed directly above the site where a 50 ul bolus of GFP (2 mg/ml dna plasmid in PBS) was injected intradermally. The intensity of expression of the GFP is substantial where only four spark discharges were administered. Similar results were obtained where eight spark discharges were administered.

B. Single Polarity Non-Invasive Tissue Contacting Array

A device including a Van de Graaff generator and a non-invasive single polarity tissue contacting 4 by 4 array to deliver either 4 or 8 pulses to tissue was obtained. Guinea pigs were obtained and treated in four repeat experiments by a 50 ul bolus intradermal injection of GFP (2 mg/ml dna plasmid in PBS) followed by pulsing the tissue surface using the single polarity contact electrode (30 kVolts, gap of 1 cm, 4 to 8 pulses of about 25 milliJoules energy). The pulses were effectively pulsed to the array wherein each needle or pin received an equivalent charge to dissipate into the tissue. The GFP was successfully electroporated into the epidermal tissues whether 4 pulses or 8 pulses were administered.

C. Single Polarity Invasive Tissue Contacting Electrode

A device including a Van de Graaff generator and a tissue penetrating electrode was tested in guinea pigs using 280 ul of 0.1 mg/ml GFP delivered in a single bolus via delivery into the tissue from the tissue penetrating electrode itself. The single spark onto an invasive electrode provided sites of electroporation to the tissue cells.

D. Electropermeabilization System Using Piezoelectric Crystal

A device comprising a piezoelectric crystal as a power source and a contact electrode array is placed 1 cm above a mammalian tissue surface and is pulsed with either 4 or 8 spark discharges across the 1 cm gap and above a 50 ul (microliter) bolus that is previously delivered by intradermal injection of green florescent protein (2 mg/ml dna plasmid in PBS) expressing plasmid (plasmid pgw12-GFP from Aldevron, N. Dakota). This gap should result in repeated sequence of 4 or 8 sparks, resulting in delivery of approximately 25 milliJoules of energy during each spark event. If electropermeabilization has taken place and the plasmid entered the cells in the epidermal tissue, the protein encoded by the plasmid will be expressed and the green florescent protein will fluoresce under UV light.

Application of the methods and devices described herein are well suited for cellular delivery of therapeutic molecules to cells for eliciting immune responses or for other treatments. This technology is well suited for DNA based vaccine delivery and for gene-based therapies. For example, a therapeutic amount of substance comprising a polynucleotide encoding an antigen polypeptide or a formulation of the polynucleotide and biologic salts as one of skill in the pharmaceutical arts is well versed, can be injected into epidermal, dermal, or subdermal tissues followed by delivery to the tissue of a discharge of electric energy from the device via either the non-contact electrode or alternatively the singular polarity tissue contacting array, and the injected polynucleotide will be electroporated into the cells of that tissue. Moreover, the use of the spark-gap method allows for electropermeabilization of targeted tissue, specifically the upper most layers of the skin tissues. GFP expression only occurs in the top most layers of the skin.

Immune Experiment

Figure 9:
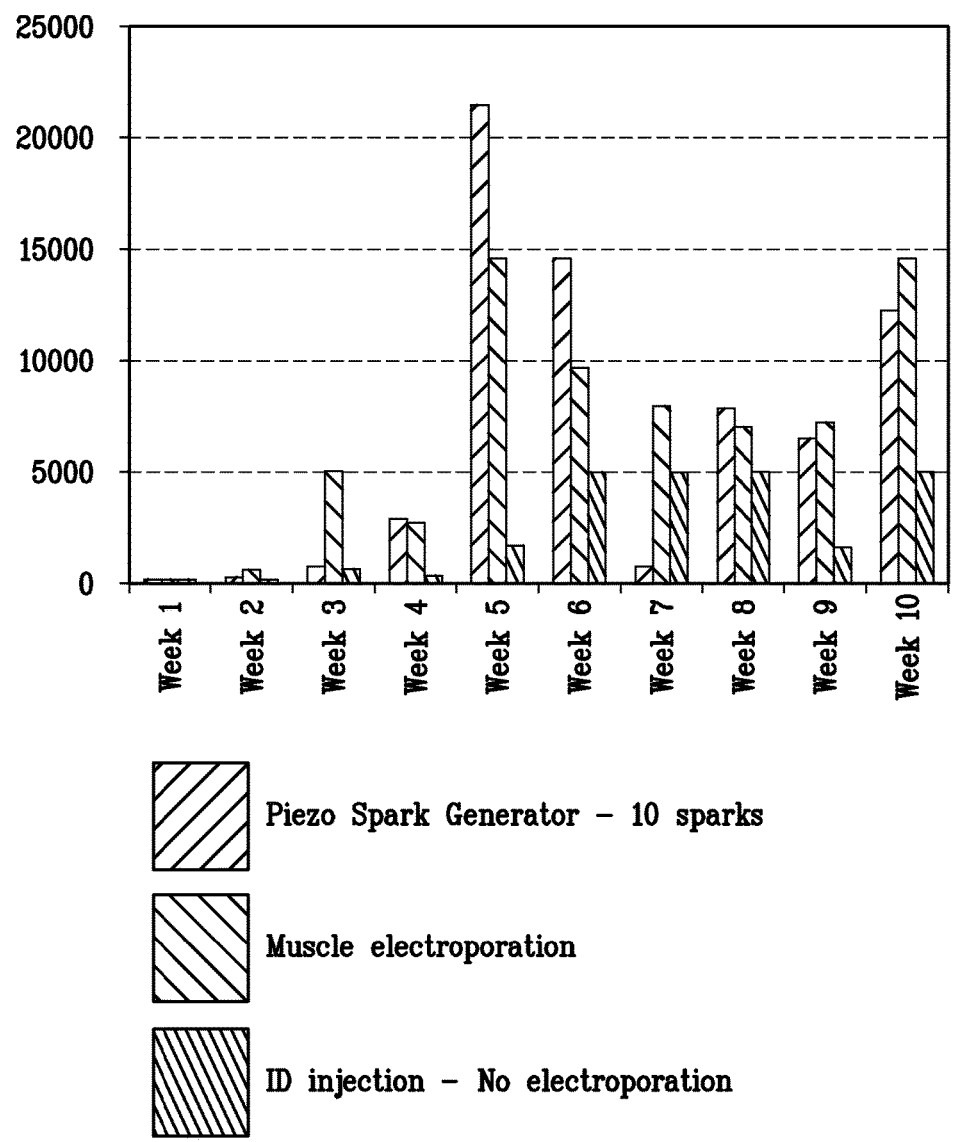
FIG. 9 is a graph showing titers of antibodies to influenza protein (NP) following dermal injection and pulsed using the spark-gap method of the disclosure.

In further experiments, animals injected with influenza antigen (NP) and pulsed using the apparatus, were studied for the expression of antibodies to the antigen. Specifically, the test animals (guinea pigs) were given intradermal injections of the antigen (50 ul bolus comprising 1 mg/ml NP plasmid) followed by electropermeabilization using the spark-gap apparatus (each animal receiving 10 sparks per injection site). Titers were followed out to ten weeks as shown in FIG. 9, which is a graph showing titers of antibodies to influenza protein (NP) following dermal injection and pulsed using the spark-gap method. The data of the spark-gap pulsed animals is compared to immune response elicited from delivery of antigen to muscle pulsed using a non spark-gap system, and to dermal injection of antigen without pulsing as control. The animals were boosted with an injection of antigen at week 4. Titers reached significant levels by week 5. These titers were superior to those logged for muscle delivered and electroporated antigen.

While embodiments may have many different forms, there is shown in the drawings and as herein described in detail various implementations with the understanding that the present disclosure is to be considered exemplary and is not intended to limit the invention to the embodiments illustrated. The scope of the invention will be measured by the appended claims and their equivalents.

All of the compositions and methods disclosed and claimed herein can be made and executed without undue experimentation in light of the present disclosure. While the compositions and methods have been described in terms of various implementations, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The implementations illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by various implementations and optional features, modification and variation of the concepts herein disclosed may be resorted to by those skilled in the art, and that such modifications and variations are considered to be within the scope of this invention as defined by the appended claims.

What is claimed is:

1. A device for delivering an electropermeabilizing electric pulse to a surface of a mammalian tissue, comprising:
   an energy source that is capable of generating at least a sufficient electrical potential between 0.9 kVolts to 109 kVolts, wherein the energy source of electrical potential is selected from the group consisting of a 1 V battery, a 3 V battery, a 9 V battery, a 12 V battery, piezoelectric crystal, a charge coil, a van de Graaff generator, and a charged capacitor;
   a non-contact electrode;
   a lead wire electrically coupled to the energy source and a receiving wire electrically coupled to the non-contact electrode, wherein the lead wire and the receiving wire are within a spark gap regulator housing and electrically isolated from one another and have a first space gap between the lead wire and the receiving wire, wherein the first space gap has a first predetermined distance and operates as a spark gap regulator; and
   a housing for the energy source, the lead wire, the receiving wire and the non-contact electrode,
   wherein a distal end of the housing extends distally beyond a distal end of the non-contact electrode by a second predetermined distance, the second predetermined distance defining a second space gap between the distal end of the non-contact electrode and the distal end of the housing;

wherein the device is configured such that, when the distal end of the housing abuts the surface of the mammalian tissue and the sufficient electric potential is generated, the electropermeabilizing electric pulse jumps the second space gap to the surface of the mammalian tissue in a manner reversibly porating cells of the surface of the mammalian tissue without causing macroscopic damage to an integrity of the surface of the mammalian tissue; wherein the second predetermined distance is constant, and the first predetermined distance is equal to or greater than the second predetermined distance.

2. The device of claim 1, wherein the first predetermined distance is between 0.01 cm and 4 cm.

3. The device of claim 1, wherein the non-contact electrode is a single polarity electrode.

4. The device of claim 3, wherein the single polarity electrode has a shaped form, the shaped form comprising spherical, pointed or flat shape.

5. The device of claim 1, wherein the spark gap regulator housing of the lead wire and receiving wire comprises an electrically inert material.

6. The device of claim 1, wherein the non-contact electrode carries a voltage potential having a total electric charge of about between $2.8 \times 10E-8$ and $2.5 \times 10E-6$ Coulombs.

7. The device of claim 1, wherein the non-contact electrode is configured to impart to the surface of the mammalian tissue a total energy discharge of between about 0.000025 and about 0.27 Joules.

8. The device of claim 1, wherein the energy source is capable of generating electric pulses having a time length about between 5 nanoseconds and 5 microseconds.

9. The device of claim 1, wherein the energy source is capable of generating electric pulses a multiplicity of times between 2 and 20 pulses.

10. The device of claim 1, wherein the energy source is capable of generating an electric voltage potential over a period of time less than 1 millisecond.

11. The device of claim 10, wherein the period of time is less than 100 microseconds.

12. The device of claim 10, wherein the energy source is a piezoelectric crystal.

13. The device of claim 1, wherein the first predetermined distance is greater than the second predetermined distance.

* * * * *